(12) United States Patent
Hu

(10) Patent No.: US 6,229,869 B1
(45) Date of Patent: May 8, 2001

(54) TILTED GANTRY IMAGE CORRECTION FOR A MULTISLICE COMPUTED TOMOGRAPHY SYSTEM

(75) Inventor: Hui Hu, Waukesha, WI (US)

(73) Assignee: General Electric Company, Schnectady, NY (US)

(*) Notice: Subject to any disclaimer, the term of this patent is extended or adjusted under 35 U.S.C. 154(b) by 0 days.

(21) Appl. No.: 09/140,131

(22) Filed: Aug. 25, 1998

(51) Int. Cl.$^7$ .................................................. H61B 6/03
(52) U.S. Cl. ................................. 378/4; 378/15; 378/901
(58) Field of Search .......................... 378/4, 15, 20, 378/901

(56) References Cited

U.S. PATENT DOCUMENTS

| | | |
|---|---|---|
| 4,088,888 | * 5/1978 | Brook et al. |
| 5,740,222 | * 4/1998 | Fujita et al. ............................ 378/4 |
| 5,799,054 | * 8/1998 | Hum et al. ............................ 378/177 |

* cited by examiner

*Primary Examiner*—David V. Bruce
(74) *Attorney, Agent, or Firm*—Armstrong Teasdale LLP; Christian G. Cabou (57) ABSTRACT

The present invention allows for accurate reconstruction of images based on multislice CT system scans using a tilted gantry. The present invention comprises a system and method for shifting the center of rotation of a reconstructed image into alignment with a longitudinal patient axis based on the tilt angle value. The present invention provides an algorithm to determine an offset amount for aligning the image. The offset amount is determined from a plurality of raw projection data used to formulate the image. The offset amount is provided for both axial and helical scanning and allows the reconstruction of an accurate image. Additionally, the system and method of the present invention provide a table speed offset and an indexing offset to account for the discrepancy in thickness of the x-ray beam at the longitudinal patient axis between tilted and non-tilted scans.

22 Claims, 4 Drawing Sheets

TILTED GANTRY IMAGE CORRECTION FOR A MULTISLICE COMPUTED TOMOGRAPHY SYSTEM

BACKGROUND OF THE INVENTION

The present invention relates generally to computed tomography systems, and more particularly, to image reconstruction when performing a scan with a tilted gantry using a multislice computed tomography system.

In a typical CT system configuration, an x-ray source projects a fan-shaped beam which is collimated to lie within an X-Y plane of a Cartesian coordinate system and generally referred to as the "imaging plane." The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element or cell of the array produces a separate electrical signal that is a measurement of the beam attenuation at that detector location. The attenuation measurements from all the detector cells are acquired separately to produce a transmission profile.

In typical CT systems, the x-ray source and the detector array are rotated with a gantry within the imaging plane and around the object to be imaged so that the rotational angle at which the x-ray beam intersects the object constantly changes. A group of x-ray attenuation measurements, i.e., projection data, from the detector array at one gantry rotational angle is referred to as a "view." A "scan" of the object comprises a set of views made at different gantry rotational angles, or view angles, during one revolution of the x-ray source and detector. In a scan, the projection data is processed to construct an image that corresponds to a two dimensional slice taken through the object. This process is called image reconstruction, and there are many image reconstruction techniques. One such method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display and hence produce the image.

Image slices typically are acquired so that each slice is perpendicular to a longitudinal axis of the patient, i.e., the slices are substantially parallel to each other and spaced in the z direction. It often is preferable to acquire slices at a non-perpendicular orientation, however, to better visualize certain structures within the patient. For example, slices at angles other than 90 degrees to the longitudinal axis of the patient, i.e., non-transverse slices, are preferable when studying certain internal organs.

To provide such an angular orientation, the gantry of the system is tilted so that the axis of rotation of the x-ray source, or the gantry axis, is inclined relative to the axis of the patient. The gantry is tilted about a pivot point so that the gantry may be positioned at different tilt angles. An encoder or some other transducer is coupled to the gantry to detect the tilt angle. The angular orientation (theta) of the gantry about the pivot point, as indicated by the encoder or transducer, is supplied to a control processor that is programmed to control operation of the system.

Utilizing a tilted gantry to obtain images is problematic, however, in a CT system having multiple rows of detectors in the z-direction, known as a "multislice" system. The projection data acquired by a multislice system comprises data having different centers of rotation, due to the multiple rows of detectors in the z-direction. Typical image reconstruction methods, however, assume the data has the same center of rotation. Upon reconstruction of the image from the projection data using current systems, the different centers of rotation cause the image center to be shifted up or down.

Further, for axial CT scans, also known as stop-and-shoot scans, further error is introduced into a multislice system by the current table indexing methods. Present systems advance the table for each slice by the thickness of the x-ray beam in the z-direction. With a tilted gantry and multiple rows of detectors, however, this table indexing results in uneven slice spacing.

Additionally, current image reconstruction techniques create problems for helical CT scans using a tilted gantry. In a helical CT scan, the table constantly moves the patient in the z-direction at a specified speed while the data for the prescribed number of slices is acquired. Such a scan generates a single helix from a one fan beam helical scan, or in the case of multislice systems, multiple helixes. The helix mapped out by a fan beam yields projection data from which images in each prescribed slice may be reconstructed. In a multislice system, portions of projection data from multiple fan beams may be utilized to reconstruct a single slice. The differing centers of rotation for each portion of the data used to reconstruct the image cause artifacts and other image errors for a multislice system. Further, some current multislice systems combine projection data prior to the filtered back projection operation, mentioned above, to increase reconstruction speed. Combining projection data having differing centers of rotation, however, causes artifacts and other image errors in the reconstructed image.

Thus, utilizing current reconstruction techniques with a multislice system having a tilted gantry results in artifacts and other unacceptable defects in the image. Yet, implementing special, new reconstruction techniques only for tilted gantry scans in a multislice system would be time consuming, expensive and would create exceptions to the current standard techniques. Therefore, it is desirable to maintain the current reconstruction techniques and integrate them with multislice systems to produce images of equivalent quality.

BRIEF SUMMARY OF THE INVENTION

The present invention provides a system and method for the accurate reconstruction of tilted gantry images comprising projection data having different centers of rotation relative to a longitudinal patient axis. According to the present invention, a computerized tomography system comprises a gantry having an aperture adapted to encircle an imaging object, and including an x-ray source and an opposing detector array each rotateably mounted on opposite sides of the aperture. A plane between the x-ray source and the detector array forms a gantry plane that is positionable along a longitudinal axis of the object. The frame is adapted for tilt displacement of the gantry plane at a tilt angle relative to the longitudinal axis. The x-ray source is rotateable about an axis of rotation perpendicular to the tilt angle and is capable of emitting x-rays from a focal spot at a each of a plurality of views corresponding to a combination of a rotational angle value and an associated tilt angle value. The detector array has a plurality of detector elements forming a plurality of fan beam planes between each of the plurality of detector elements and the x-ray source. Each of the plurality of fan beam planes has a center of rotation value along the axis of rotation. Each of the plurality of detector elements is capable of receiving the emitted x-rays at each of the plurality of views and providing raw projection data indicating the intensity of the x-rays received at each of the plurality of views.

Additionally, the system includes a computer system in communication with the detector array. The computer system has a memory to store data including data representative of the raw projection data, and the rotational angle value, the tilt angle value, and the center of rotation value corresponding to the raw projection data. The computer system further includes program signals representative of an algorithm for constructing image data from the raw projection data. The algorithm shifts the center of rotation values associated with the image data by an offset amount that is a function of the tilt angle so that the image data is centered about the longitudinal axis of the object.

The offset amount can be defined as $Y\_shift = d_{FB} \times \tan(\theta)$, where $d_{FB}$ is the distance along the axis of rotation between the gantry plane and the fan beam plane corresponding to the raw projection data associated with the image data; and $\theta$ is the tilt angle value corresponding to the raw projection data associated with the image data.

The computer system may further comprise program signals representative of an algorithm for error correction of the raw projection data to provide corresponding corrected projection data. The algorithm further reconstructing the corrected projection data to provide the image data.

The algorithm may shift the center of rotation values associated with the image data associated with each of the plurality of fan beam planes by the offset amount to align the relative position of each of the plurality of the image data. Alternatively, the algorithm may shift the center of rotation values of the projection data by the offset amount.

The computer system may further comprise signals representative of an algorithm that advances the imaging object through the aperture in indexing steps that are a multiple of a thickness of a slice of the image data, where the indexing step, denoted as D_t, defined by: $D\_t = t/\cos\theta$; where t is the thickness of the slice of the image data and $\theta$ is the tilt angle value.

The detector array may further comprise a plurality of channels each at an angular displacement about the aperture relative to the x-ray source. The computer system further comprises program signals representative of an algorithm for error correction of the raw projection data and provides corresponding corrected projection data The algorithm further weights the corrected projection data by a weighting function to provide weighted projection data, where the algorithm further combines a plurality of the weighted projection data corresponding to a plurality of the views and a plurality of the fan beam planes to form a weighted sum data. And the algorithm further reconstructs the weighted sum data to provide the image data. The algorithm may shift the center of rotation value of each of the corrected projection data by the offset amount. The offset amount may be defined as: $Y\_shift = d_{FB}*\tan(\theta)$; where: $d_{FB}$=distance along the axis of rotation between the gantry plane and the fan beam plane corresponding to the raw projection data associated with the image data; and $\theta$=the tilt angle value corresponding to the raw projection data associated with the image data.

The system may further comprise a table capable of moving the imaging object through the aperture at a table feeding speed, s, per rotation of the x-ray source about the aperture. The offset amount shifts the corrected projection data along the channel direction for each the view and each the channel, The offset amount is:

$$det\_shift = \mathrm{atan}\{(\sin(\beta)*Y0\_shift)/L_{fb} - (\cos(\beta)*Y0\_shift)\}/det\_dgamma$$

where:
$\beta$=the rotational angle value;
$L_{fb}$=distance from the focal spot of the x-ray source to the axis of rotation;
det_dgamma=the angular increment of the detector channel;

$$Y0\_shift = Y\_shift + F\_shift$$

where:

$$Y\_shift = d_{FB} \times \tan(\theta)$$

where:
$d_{FB}$=distance along the axis of rotation between the gantry plane and the fan beam plane corresponding to the raw projection data associated with the image data;
$\theta$=the tilt angle value corresponding to the raw projection data associated with the image data; and $$F\_shift = [-n, -n+1, \ldots n-1, n]*\{(\Delta\beta)/(2\Pi)\}*(s)*\tan(\theta).$$

The computer system may further comprises signals representative of an algorithm that advances the imaging object through the aperture at the table speed, s, defined by: $s = (p*\cos\theta)/t$; where: p=helical pitch; $\theta$=the tilt angle value corresponding to the raw projection data associated with the image data; and t is the thickness of a slice of the image data at the longitudinal patient axis.

Similarly, the present invention discloses a method of compensating for a gantry tilt angle when obtaining computed tomography images from a multiple fan beam detection system. The method comprising acquiring image data comprising a plurality of projection data representing an imaging object's attenuation of x-rays emitted from an x-ray source and received by a detector array, where the x-ray source rotates about an aperture encircling the imaging object and about an axis of rotation perpendicular to a plane of the gantry. Also, the method calls for acquiring data representing the center of rotation values corresponding to the projection data and adjusting the positioning of the image data by an offset amount that is a function of the center of rotation values and the tilt angle value.

Further, the method may include acquiring a value, $d_{FB}$, for the distance along the axis of rotation between a plane of the gantry and a fan beam plane corresponding to the projection data associated with the image data; and determining the offset amount: $Y\_shift = d_{FB}*\tan(\theta)$; where $\theta$ is the tilt angle value corresponding to the projection data associated with the image data.

The method may further comprise acquiring corrected projection data based on an applied error correction value for each of the projection data, and reconstructing the corrected projection data to provide the image data. The adjusting step shifts the center of rotation value of the image data associated with each detector fan beam by the offset amount to align the relative position of each of the image data. Alternatively, the adjusting step shifts the center of rotation value of each of the plurality of projection data by the offset amount.

The method may comprise advancing the imaging object through the aperture in indexing steps that are a multiple of the thickness of a slice of the image data. The indexing step value, denoted as D_t, defined by: D_t=t/cos θ, where t is the thickness of a slice of the image data and θ is the tilt angle value.

Additionally, the method may include acquiring corrected projection data based on an applied error correction value for each of the plurality of projection data. Each of the corrected projection data having a corresponding view value representative of the rotational angle of the x-ray source and a corresponding channel value representative of an angular displacement of a channel of the detector array relative to the x-ray source. The method includes weighting the corrected projection data by a weighting function to provide weighted projection data. The method combines a plurality of the weighted projection data having a plurality of associated view angle values and associated with a plurality of the detector fan beam planes to form a weighted sum data. And, the method involves reconstructing the weighted sum data to provide the image data.

This method may comprise determining a helical pitch, p, determining a thickness, t, of a slice of the image data at a longitudinal axis of the imaging object, and advancing the imaging object through the aperture at a speed, s, defined by: s=(p*cos θ)/t; where θ is the gantry tilt angle value corresponding to the raw projection data associated with the image data.

Yet further, the method may comprise acquiring a value, $d_{FB}$, for the distance along the axis of rotation between a plane of the gantry and the detector fan beam plane corresponding to the projection data associated with the image data. Next, the method involves acquiring a tilt angle value θ corresponding to the projection data associated with the image data and determining the offset amount: Y_shift= $d_{FB}$*tan(θ).

Additionally, the method further comprises advancing the imaging object through the aperture at a speed, s, per rotation of the x-ray source about the aperture. In this case, the detector array further comprises a plurality of channels. And the method involves determining the offset amount that shifts the corrected projection data along the channel direction for each view and each channel, where the offset amount value is:

$$\text{det\_shift} = \text{atan}\ \{(\sin(\beta)*\text{Y0\_shift})/L_{fb} - (\cos(\beta)*\text{Y0\_shift})\}/\text{det\_dgamma}$$

where:
  β=the rotational angle value;
  $L_{fb}$=distance from the focal spot of the x-ray source to the axis of rotation;
  det_dgamma=the angular increment of the detector channel;

Y0_shift=Y_shift+F_shift where:

Y_shift=$d_{FB}$×tan(θ)

where:
    $d_{FB}$=distance along the axis of rotation between the gantry plane and the fan beam plane corresponding to the raw projection data associated with the image data;
    θ=the tilt angle value corresponding to the raw projection data associated with the image data; and F_shift=[−n, −n+1, ... n−1, n]*{(Δβ)/(2Π)}*(s)*tan(θ).

DETAILED DESCRIPTION OF THE INVENTION

Figure 1:
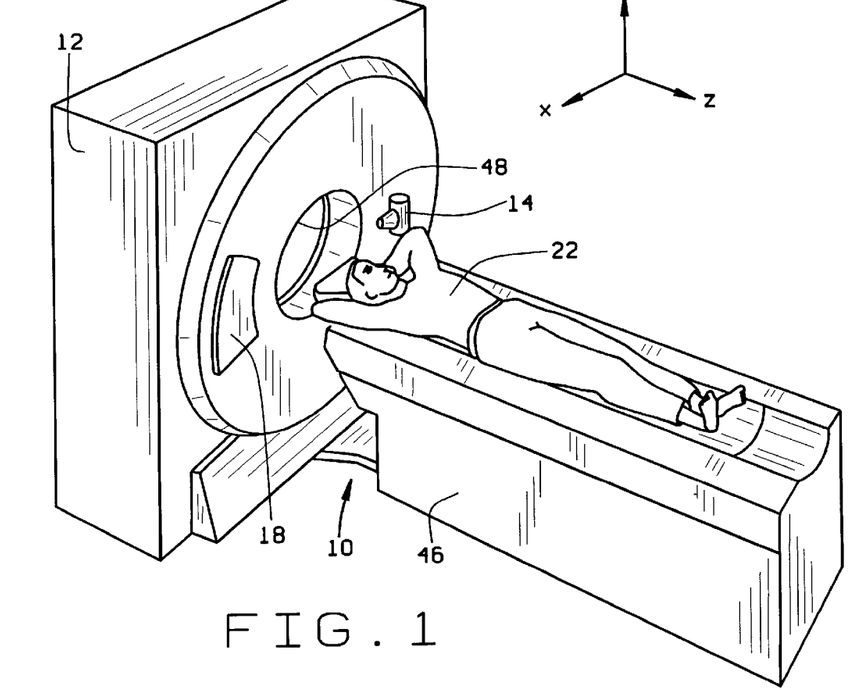
FIG. 1 is a pictorial view of a CT imaging system.
Figure 2:
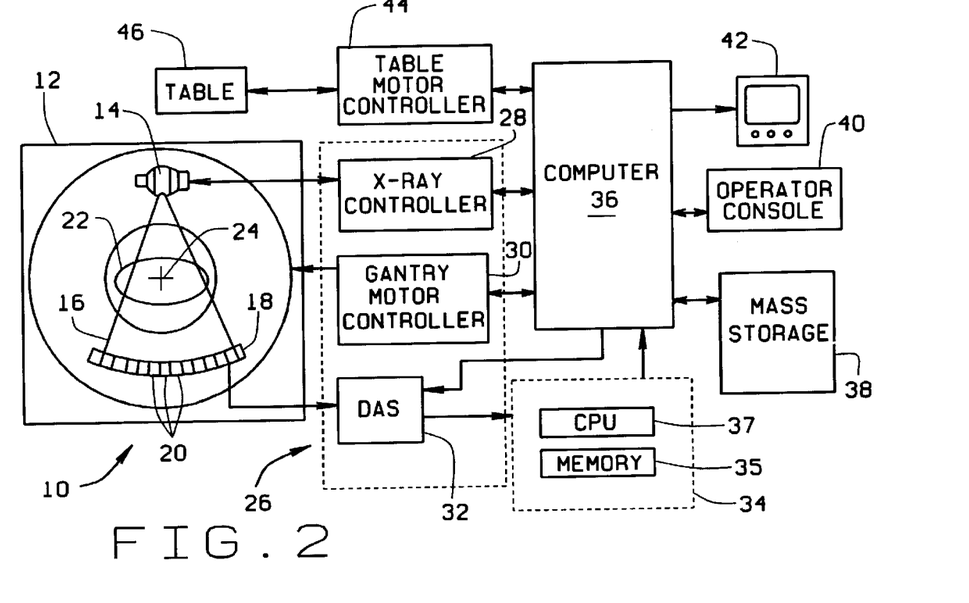
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is divided into channels formed by detector elements 20 which together sense the projected x-rays that pass through a medical patient 22 or other imaging object. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about an axis of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog projection data from detector elements 20 and converts the analog data to digital projection data for subsequent processing. An image reconstructor 34 receives into its memory 35 the digitized x-ray projection data from DAS 32 and comprises a processor 37 that performs the high speed image reconstruction algorithm as defined by the program signals stored in the memory. The reconstructed image is applied as an input to a computer 36 which stores the image in a mass storage device 38.

During a scan, gantry 12 often is tilted with respect to the z-axis. A driving mechanism (not shown) tilts gantry 12 about a pivot point (not shown) so that axis of gantry rotation 24 is not parallel to the z-axis. An encoder (not shown) is coupled to gantry 12 detects the tilt angle θ, i.e., the amount of gantry tilt about the pivot point, and generates pulses indicative of the angular orientation, θ, of the gantry about the pivot point. The output of the encoder is coupled, for example, to computer 36 or gantry motor controller 30.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. For an axial scan, also known as a stop-and-shoot scan, table 46 indexes patient 22 to a location, and allows gantry 12 to rotate about the patient at the location. In contrast, for a helical scan, table 46 moves patient 22 through aperture 48 at a table speed, s, equal to a displacement along the z-axis per a rotation of gantry 12.

Figure 3:
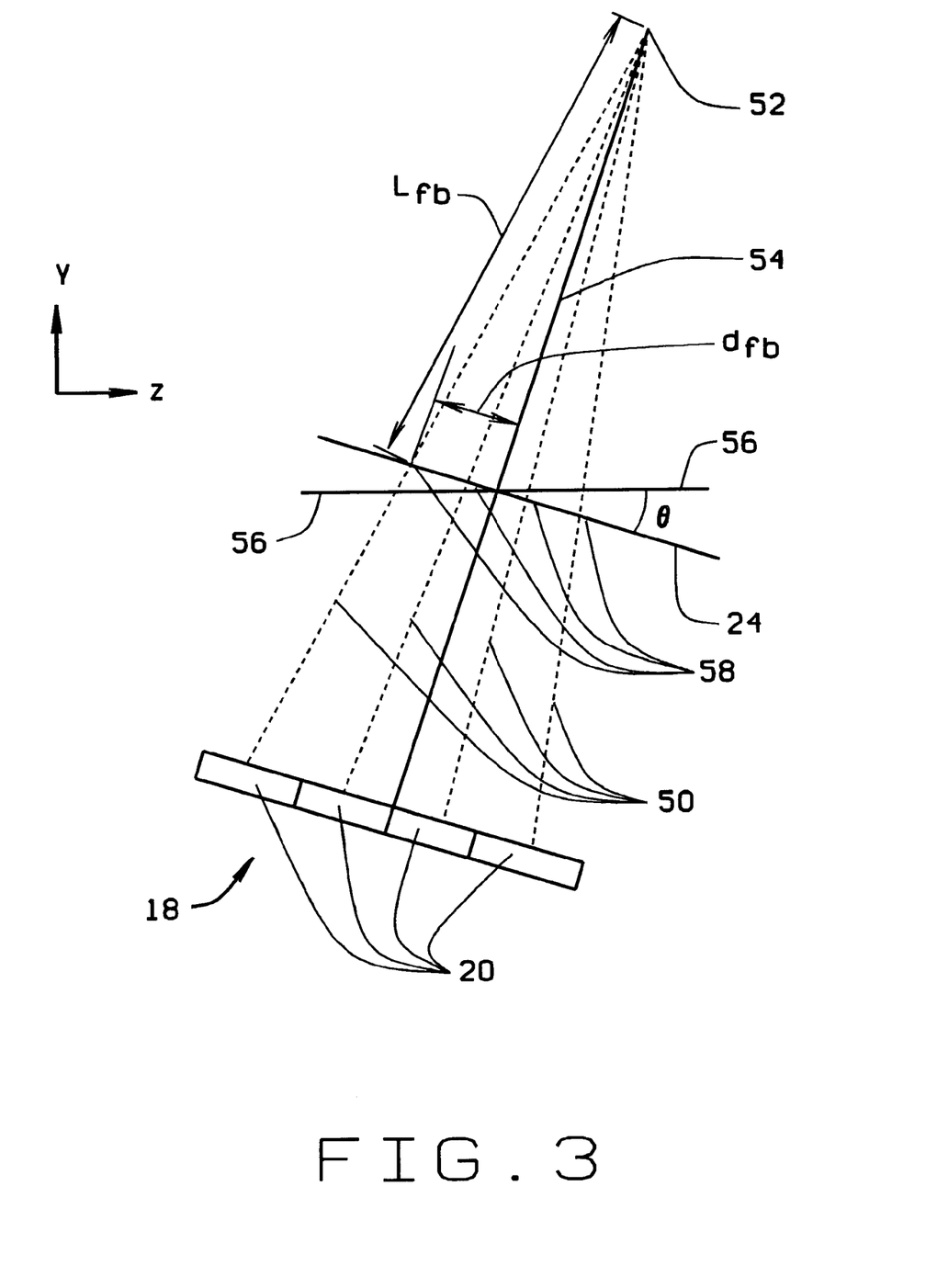
FIG. 3 is a representation of the relationship between a longitudinal patient axis and an axis of rotation of a detector array when the gantry of the CT imaging system is tilted.

As shown in FIG. 3, four fan beam planes 50 are defined between four rows of detectors 20 and a focal spot 52 of x-ray source 14. The gantry plane 54 carrying x-ray source 14 and detector array 18 is angularly displaced from a vertical position at a tilt angle θ, causing axis of rotation 24 to be similarly angularly displaced from a longitudinal patient axis 56. Each of the four fan beams 50 is displaced a distance $d_{fb}$ along the axis of rotation 24 from gantry plane 54 to its own isometric center of rotation 58. Thus, when gantry 12 is tilted, isometric center of rotation 58 for each fan beam 50 is displaced from longitudinal patient axis 56 by some isometric offset amount, $off_{fb}$.

Offset amount, $off_{fb}$, for the center of rotation 58 of each fan beam 50 creates problems in image reconstruction using typical reconstruction techniques. Typical systems for both axial and helical scanning assume that axis of rotation 24, and hence center of rotation 58 for each fan beam 50 coincides or is parallel to longitudinal patient axis 56. Examples of image reconstruction algorithms that may be used for reconstructing an image from helical scan data are disclosed in U.S. Pat. No. 5,559,847, U.S. Pat. No. 5,541,970, and U.S. Pat. No. 5,606,585, each assigned to the assignee of the present invention and hereby incorporated by reference. Utilizing a tilted gantry 12 with these systems causes the image centers to be shifted relative to longitudinal patient axis 56. This shifting may cause artifacts and other errors in the reconstructed image.

Figure 4A:
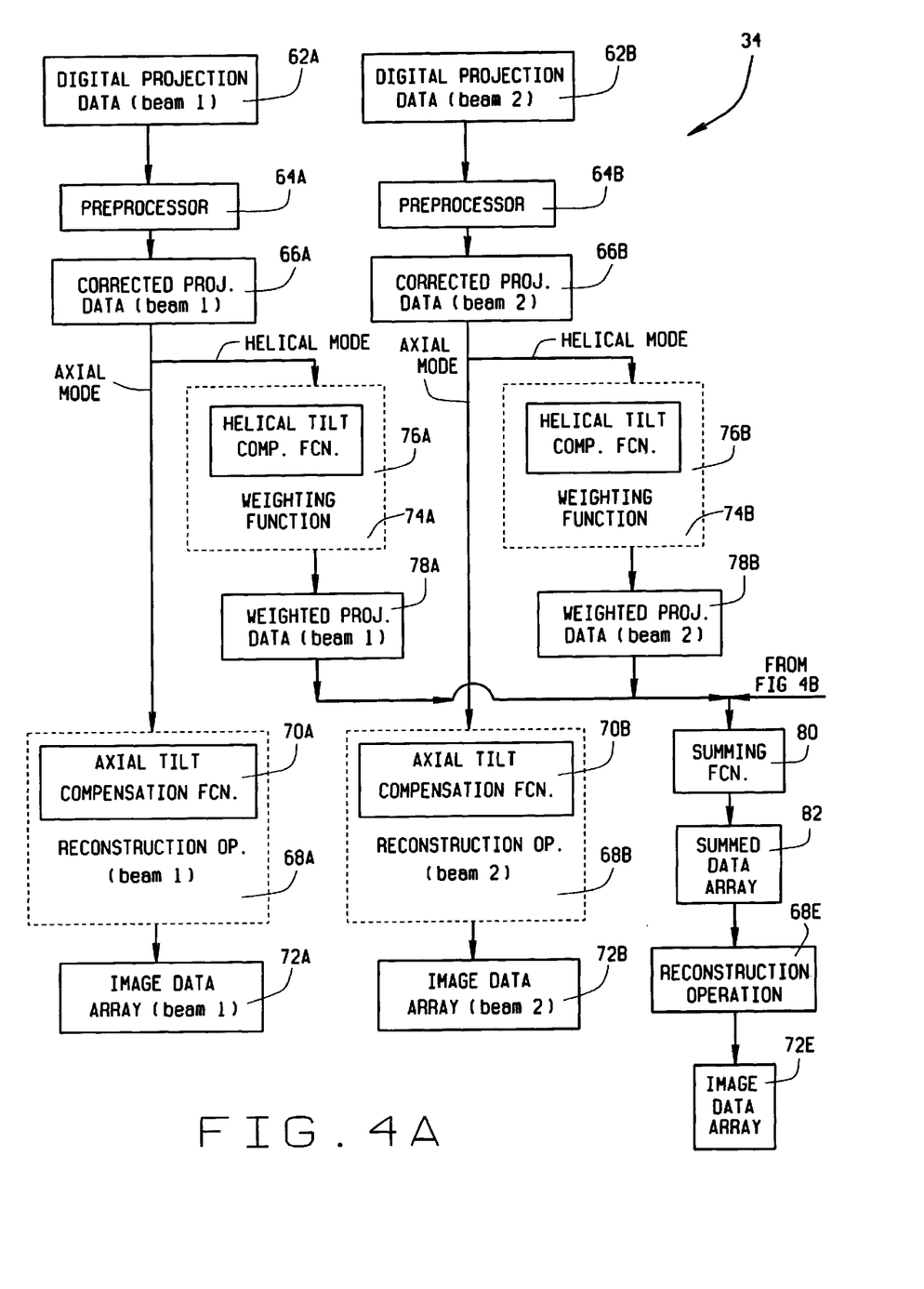
FIGS. 4A and 4B together form a block diagram of an image reconstructor that forms part of the CT imaging system of the present invention.
Figure 4B:
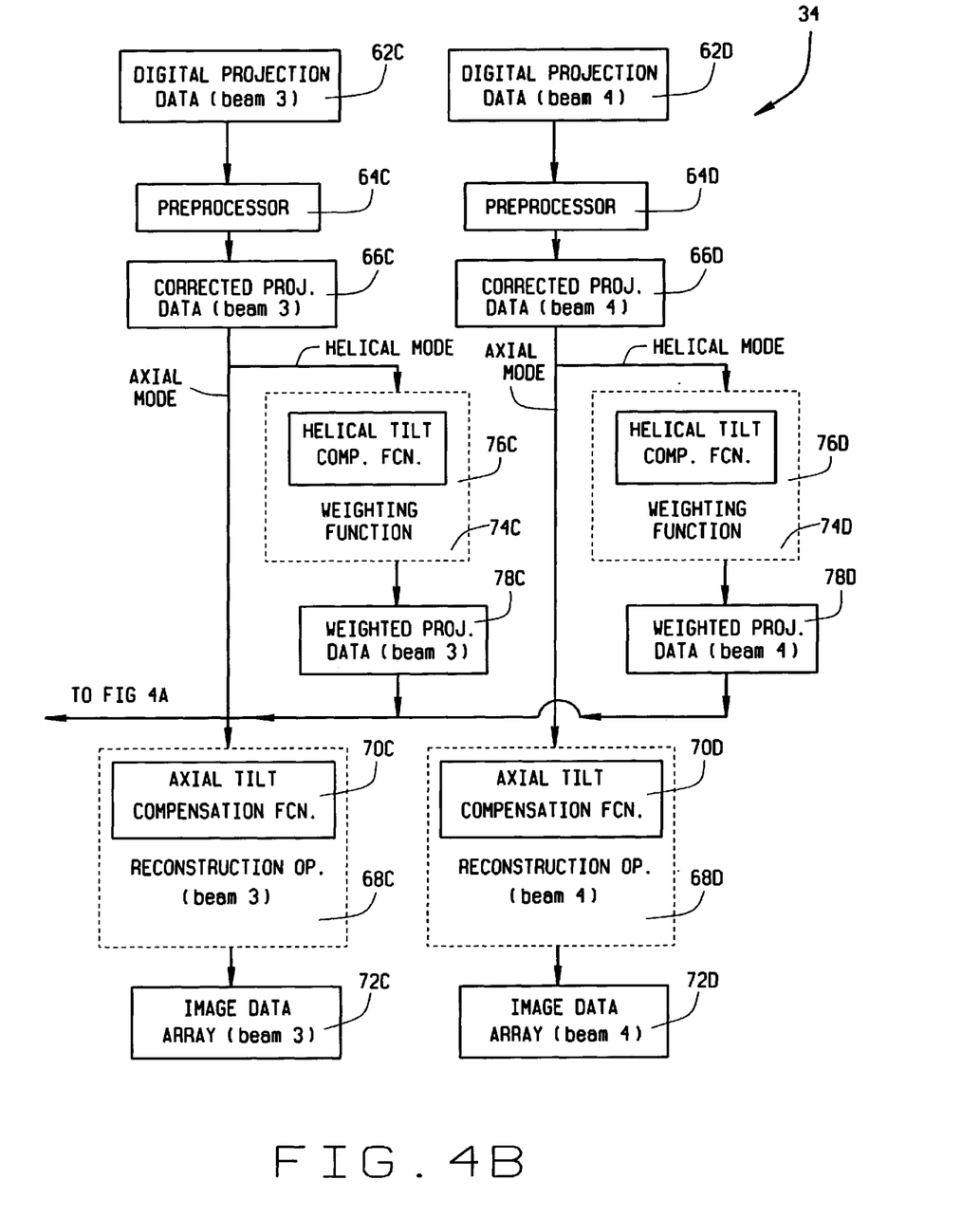

Referring to FIGS. 4A and 4B, the present invention comprises image reconstructor 34 that provides tilt-compensated image data 60A–D from raw projection data array 62A–D having different centers of rotation 58. Image reconstructor comprises memory 35 (FIG. 2) for storing various data and signals representative of various algorithms, as is discussed below. Particularly, each view of raw digital data array 62A–D from DAS 32 for each fan beam is received at respective preprocessors 64A–D, where the respective beam is preprocessed to correct for various well-known errors such as beam hardening, offsets and variations in detector and channel gain. Also, the negative logarithm is taken to provide corrected projection data array 66A–D.

For an axial scan, also known as a step-and-shoot scan, each corrected projection data array 66A–D is input to a reconstruction operation or algorithm 68A–D that utilizes an axial tilt compensation function or algorithm 70A–D to produce an image data array 72A–D for each fan beam.

For a helical scan, corrected projection data array for each beam 66A–D is input into a corresponding weighting operation or algorithm 74A–D that utilizes a helical tilt compensation function or algorithm 76A–D to provide weighted and tilt compensated projection data. The weighted projection data is written into a corresponding location in weighted projection data array 78A–D. Each weighted projection data array 78A–D is summed 80 to provide a summed data array 82. Specifically, for the same view, the magnitude of each pixel in beam 1 array is summed with the magnitude of the corresponding pixels in the beam 2, beam 3 and beam 4 arrays. Summed data array 82 is then utilized in a reconstruction operation or algorithm 68E to produce an image data array 72E. The resulting image arrays 72A–E may be stored for later use or displayed to the operator.

As mentioned above, tilt compensation is required to correct for using projection data having different centers of rotation. This leads to the following two problems in reconstruction. First, intrinsic to multislice CT, the iso-centers 58 of different detector rows, corresponding to each fan beam plane 50, shift relative to the patient axis by Y_shift, where $$Y\_shift = d_{fb} * \tan(\theta) \quad (1)$$

For example in a 4×5 mm scan, if the gantry is tilted 30° and the two most distant fan beams are ±7.5 mm from gantry plane 54, then the largest shift is Y_shift=±7.5*tan(30°)= ±4.33 mm. Or, for a 2×10 mm scan with a tilt angle 30° and the two most distant fan beams are ±5.0 mm from gantry plane 54, then the largest shift is Y_shift=±5*tan(30°)= ±2.89 mm. Thus, the largest relative shift (from the top and bottom detector rows) is 8.66 mm for 4×5 or 5.78 mm for 2×10. Note that Y_shift is the function of gantry tilt angle and $d_{fb}$. The term $d_{fb}$ is a function of the collimated thickness of x-ray beam 16, in the direction of axis of rotation 24, and detector row index. Therefore, Y_shift can be determined once these parameters are chosen.

A second, and more complex, problem occurs with gantry tilt utilized in helical CT. In helical CT, another center-shifting, F_shift, is introduced by a Z-Filtering Reconstruction method, as described in U.S. Pat. No. 5,606,585, where $$F\_shift = [-n, -n+1, \ldots n-1, n] * \{(\Delta\beta)/(2\Pi)\} * (s) * \tan(\theta) \quad (2)$$

In this equation, the n and Δβ are the parameters of a z-kernel introduced by the Z-Filtering Reconstruction method as described in U.S. Pat. No. 5,606,585. Note that F_shift is a function of gantry tilt angle, table speed per rotation, s, the filter's angular displacement and kernel term. Therefore, F_shift can be determined once these parameters are chosen.

Axial scanning using gantry 12 having a tilt angle θ contains only one kind of center-shifting—Y_shift. This shift, if not compensated, will causes isometric center 58 of image data array 72A–E to be shifted up or down relative to longitudinal patient axis 56 by Y_shift. This slice misalignment causes problems in applications such as 3D, MPR and Paging modes.

The solution for axial CT is to shift the center of images of both prospective and retrospective reconstruction by an amount equal to Y_shift, but in the opposite direction, to compensate for the intrinsic center-shifting. Referring to FIGS. 4A and 4B, the present invention advantageously provides axial tilt compensation function 70A–D, equal to Y_shift, that is utilized in reconstruction operation 68A–D to provide tilt-compensated image data array 72A–D. The tilt compensation for axial CT is exact and causes no adverse impact on IQ and reconstruction speed.

In the current fan beam based multislice helical CT reconstruction, corrected projection data 66A–D from different detector rows, corresponding to each fan beam plane 50, are combined prior to reconstruction operation 68E. This projection data combination is the key concept that provides roughly 4:1 data compression and therefore enables processing multislice data with the current fan beam reconstructing systems within current speed specifications. Unable to apply this combination means a much longer reconstruction time, four time longer, and a different data process architecture for tilted gantry reconstruction.

The present invention advantageously provides an approximate tilt compensation solution for helical CT scanning. As generally described above in reference to FIGS. 4A and 4B, to compensate for the center-shifting, the present invention shifts corrected projection data 66A–D along the channel direction (x-direction) by det_shift for each view and each detector row and each z kernel term, as shown below:

$$\text{det\_shift} = \operatorname{atan}\{(\sin(\beta)*Y0\_\text{shift})/L_{fb} - (\cos(\beta)*Y0\_\text{shift})\}/\text{det\_dgamma} \qquad (3)$$

where:

$$Y0\_\text{shift} = Y\_\text{shift} + F\_\text{shift}; \qquad (4)$$

$L_{fb}$=the distance from x-ray focal spot 52 to axis of rotation 24 (FIG. 4); and det_dgamma=the angular increment of a detector channel, $\Delta\gamma$, where $\gamma$ is the channel angle value.

In general, the shift also calls for resampling of the projection data by interpolations. Further, a sharpening kernel that acts as an edge-enhancing filter is applied in channel direction to compensate for the smoothing due to the interpolation mentioned above. The sharpening kernel may be combined with the reconstruction kernel. This tilt compensation method allows projection data to be combined prior to filtered-back projection. Thus, the data processing architecture remains the same for helical CT scans utilizing a tilted gantry.

Additionally, tilted gantry applications cause inaccuracies in image reconstruction because fan beam planes 50 do not intersect longitudinal patient axis 56 in the same place as would a non-tilted gantry application. This difference creates problems in the image reconstruction, which rely on the non-tilted gantry beam position.

In axial CT scans using a tilted gantry, there is a discrepancy between the thickness, t, of x-ray beam 16 and the slice position increment. This discrepancy creates a problem, considering that typical systems index table 46 by n times t, where n=4 or 2, for example, for a 4 or 2 slice system. Use of the typical indexing of table 46 in a multislice system results in a uneven slice spacing. With gantry tilt, the actual slice position increment in axial CT, denoted as D_t and measured along longitudinal patient axis 56, can be formulated as:

$$D\_t = (t)/\cos(\theta) \qquad (5)$$

where t is the beam thickness and $\theta$ is the gantry tilt angle value, as defined above. Therefore, D_t$\neq$t when gantry 12 is tilted. For example, in a 4×5 mode with $\theta$=30°, D_t=5/cos (30°)=5.77 mm. Similarly, for a 2×10 mode with $\theta$=30°, D_t=10/cos(30°)=11.54 mm. Thus, advancing table 46 by n times t results in a uneven slice spacing. Therefore, the table must be advanced by n times D_t instead. For example, in 4×5 mm mode with $\theta$=30°, table 46 is incremented by 23.08 mm rather than by 20 mm.

Similarly, in helical scanning the discrepancy between non-tilted and tilted gantry beam thickness, t, causes reconstruction problems. In the typical non-tilted case, reconstruction algorithms rely on a helical pitch equal to table speed divided by beam thickness. Due to the tilt angle, $\theta$, however, the helical pitch should be defined as:

$$p = (s/t)*\cos(\theta) \qquad (6)$$

where s, t, and $\theta$ are the table speed, beam thickness, and tilt angle, respectively, as defined above. For example, in 4×1.25 mm mode with 25 degree gantry tilt, 3:1 pitch helical scanning requires a table speed of 4.15 mm/rotation rather than 3.75 mm/rotation. Thus, the system of the present invention provides a table speed and indexing offset to account for the discrepancy in thickness, t, of x-ray beam 16 at longitudinal patient axis 56 between tilted and non-tilted scans.

Thus, the system and method of the present invention provide tilt compensation that greatly reduces image blurring. As a result, the system and method of the present invention allow the use of tilted gantry scans while providing high image quality and without any significant, adverse impact on reconstruction time. Therefore, the present invention provides for the accurate reconstruction of tilted gantry images comprising projection data having different centers of rotation relative to the longitudinal patient axis.

Although the invention has been described with reference to these preferred embodiments, other embodiments can achieve the same results. Variations and modifications of the present invention will be apparent to one skilled in the art and the following claims are intended to cover all such modifications and equivalents.

What is claimed is:

1. A computerized tomography system, comprising:

a gantry having an aperture adapted to encircle an imaging object, and including a rotateably mounted x-ray source and an opposing detector array, a plane between said x-ray source and said detector array forming a gantry plane that is positionable along a longitudinal axis of said object, said frame adapted for tilt displacement of said gantry plane at a tilt angle relative to said longitudinal axis;

said x-ray source rotateable about an axis of rotation perpendicular to said tilt angle and capable of emitting x-rays from a focal spot at a each of a plurality of views corresponding to a combination of a rotational angle value and an associated tilt angle value;

said detector array having a plurality of detector elements forming a plurality of fan beam planes between each of said plurality of detector elements and said x-ray source, each of said plurality of fan beam planes having a center of rotation value along said axis of rotation, and each of said plurality of detector elements capable of receiving said emitted x-rays at each of said plurality of views and providing raw projection data indicating the intensity of the x-rays received at each of said plurality of views; and a computer system in communication with said detector array, said computer system having a memory to store data including data representative of said raw projection data, and said rotational angle value, said tilt angle value, and said center of rotation value corresponding to said raw projection data, said computer system further including program signals representative of an algorithm for constructing image data from said raw projection data, said algorithm shifting said center of rotation values associated with said image data by an offset amount that is a function of said tilt angle so that said image data is centered about said longitudinal axis of said object.

2. A system as recited in claim 1, wherein said offset amount is:

$$Y\_\text{shift} = d_{FB} \times \tan(\theta)$$

where:

$d_{FB}$=distance along said axis of rotation between said gantry plane and said fan beam plane corresponding to said raw projection data associated with said image data; and $\theta$=said tilt angle value corresponding to said raw projection data associated with said image data.

3. A system as recited in claim 1, wherein said computer system further comprises program signals representative of an algorithm for error correction of said raw projection data and provides corresponding corrected projection data, said algorithm further reconstructing said corrected projection data to provide said image data.

4. A system as recited in claim 3, wherein said algorithm shifts said center of rotation values associated with said image data associated with each of said plurality of fan beam planes by said offset amount to align the relative position of each of said plurality of said image data.

5. A system as recited in claim 3, wherein said algorithm shifts the center of rotation values of said projection data by said offset amount.

6. A system as recited in claim 1, wherein said computer system further comprises signals representative of an algorithm that advances said imaging object through said aperture in indexing steps that are a multiple of a thickness of a slice of said image data, said indexing step, denoted as D_t, defined by:

$$D\_t = t/\cos \theta$$

where t is said thickness of said slice of said image data and θ is said tilt angle value.

7. A system as recited in claim 1, wherein said detector array further comprises a plurality of channels each at an angular displacement about said aperture relative to said x-ray source, and wherein said computer system further comprises program signals representative of an algorithm for error correction of said raw projection data and provides corresponding corrected projection data, said algorithm further weighting said corrected projection data by a weighting function to provide weighted projection data, said algorithm further combining a plurality of said weighted projection data corresponding to a plurality of said views and a plurality of said fan beam planes to form a weighted sum data, and said algorithm further reconstructing said weighted sum data to provide said image data.

8. A system as recited in claim 7, wherein said algorithm shifts the center of rotation value of each of said corrected projection data by said offset amount.

9. A system as recited in claim 8, wherein said offset amount is:

$$Y\_shift = d_{FB} * \tan(\theta)$$

where:
$d_{FB}$ = distance along said axis of rotation between said gantry plane and said fan beam plane corresponding to said raw projection data associated with said image data; and
θ = said tilt angle value corresponding to said raw projection data associated with said image data.

10. A system as recited in claim 8, further comprising a table capable of moving said imaging object through said aperture at a table feeding speed, s, per rotation of said x-ray source about said aperture, and wherein said offset amount shifts said corrected projection data along the channel direction for each said view and each said channel and said offset amount is:

$$det\_shift = \operatorname{atan} \{(\sin(62\ )*Y0\_shift)/L_{fb} - (\cos(\beta)*Y0\_shift)\}/det\_dgamma$$

where:
β = said rotational angle value;
$L_{fb}$ = distance from said focal spot of said x-ray source to said axis of rotation;
det_dgamma = said angular increment of said detector channel;

$$Y0\_shift = Y\_shift + F\_shift$$

where:

$$Y\_shift = d_{FB} \times \tan(\theta)$$

where:
$d_{FB}$ = distance along said axis of rotation between said gantry plane and said fan beam plane corresponding to said raw projection data associated with said image data;
θ = said tilt angle value corresponding to said raw projection data associated with said image data; and $$F\_shift = [-n, -n+1, \ldots n-1, n]*\{(\Delta\beta)/(2529\ )\}*(s)*\tan(\theta).$$

11. A system as recited in claim 10, wherein said computer system further comprises signals representative of an algorithm that advances said imaging object through said aperture at said table speed, s, defined by:

$$s = (p*\cos \theta)/t$$

where:
p = helical pitch;
θ = said tilt angle value corresponding to said raw projection data associated with said image data; and
t is said thickness of a slice of said image data at said longitudinal patient axis.

12. A method of compensating for a gantry tilt angle when obtaining computed tomography images from a multiple fan beam detection system, said method comprising the steps of:
(a) acquiring image data comprising a plurality of projection data representing an imaging object's attenuation of x-rays emitted from an x-ray source and received by a detector array, where the x-ray source rotates about an aperture encircling the imaging object and about an axis of rotation perpendicular to a plane of the gantry;
(b) acquiring data representing the center of rotation values corresponding to the projection data; and
(c) adjusting the positioning of the image data by an offset amount that is a function of the center of rotation values and the tilt angle value.

13. A method as recited in claim 12, further comprising the steps of:
(a) acquiring a value, $d_{FB}$, for the distance along the axis of rotation between a plane of the gantry and a fan beam plane corresponding to the projection data associated with the image data; and
(b) determining the offset amount:

$$Y\_shift = d_{FB} * \tan(\theta)$$

where θ = the tilt angle value corresponding to the projection data associated with the image data.

14. A method as recited in claim 12, further comprising the steps of acquiring corrected projection data based on an applied error correction value for each of the projection data, and reconstructing the corrected projection data to provide the image data.

15. A method as recited in claim 14, wherein the adjusting step shifts the center of rotation value of the image data associated with each detector fan beam by the offset amount to align the relative position of each of the image data.

16. A method as recited in claim 14, wherein the adjusting step shifts the center of rotation value of each of the plurality of projection data by the offset amount.

17. A method as recited in claim 12, further comprising the step of advancing the imaging object through the aperture in indexing steps that are a multiple of the thickness of a slice of the image data, the indexing step value, denoted as D_t, defined by:

$$D\_t = t/\cos\theta$$

where t is the thickness of a slice of the image data and θ is the tilt angle value.

18. A method as recited in claim 12, further comprising the steps of:
 (a) acquiring corrected projection data based on an applied error correction value for each of the plurality of projection data, each of the corrected projection data having a corresponding view value representative of the rotational angle of the x-ray source and a corresponding channel value representative of an angular displacement of a channel of the detector array relative to the x-ray source;
 (b) weighting the corrected projection data by a weighting function to provide weighted projection data;
 (c) combining a plurality of the weighted projection data having a plurality of associated view angle values and associated with a plurality of the detector fan beam planes to form a weighted sum data; and
 (d) reconstructing the weighted sum data to provide the image data.

19. A system as recited in claim 18, wherein the adjusting step shifts the center of rotation value associated with of each of the corrected projection data by the offset amount.

20. A method as recited in claim 19, further comprising the steps of:
 (a) acquiring a value, $d_{FB}$, for the distance along the axis of rotation between a plane of the gantry and the detector fan beam plane corresponding to the projection data associated with the image data;
 (b) acquiring a tilt angle value θ corresponding to the projection data associated with the image data; and
 (c) determining the offset amount:

$$Y\_shift = d_{FB} * \tan(\theta).$$

21. A method as recited in claim 18, further comprising the steps of:
 (a) advancing the imaging object through the aperture at a speed, s, per rotation of the x-ray source about the aperture, and wherein the detector array further comprises a plurality of channels; and
 (b) determining the offset amount that shifts the corrected projection data along the channel direction for each view and each channel, where the offset amount value is:

$$det\_shift = \operatorname{atan}\{(\sin(\beta)*Y0\_shift)/L_{fb} - (\cos(\beta)*Y0\_shift)\}/det\_dgamma$$

where:
 β=said rotational angle value;
 $L_{fb}$=distance from said focal spot of said x-ray source to said axis of rotation;
 det_dgamma=said angular increment of said detector channel;

$$Y0\_shift = Y\_shift + F\_shift$$

where:

$$Y\_shift = d_{FB} \times \tan(\theta)$$

where:
 $d_{FB}$=distance along said axis of rotation between said gantry plane and said fan beam plane corresponding to said raw projection data associated with said image data;
 θ=said tilt angle value corresponding to said raw projection data associated with said image data; and $$F\_shift = [-n, -n+1, \ldots n-1, n]*\{(\Delta\beta)/(2\Pi)\}*(s)*\tan(\theta).$$

22. A method as recited in claim 18, further comprising the steps of:
 (a) determining a helical pitch, p;
 (b) determining a thickness, t, of a slice of the image data at a longitudinal axis of the imaging object; and
 (c) advancing the imaging object through the aperture at a speed, s, defined by:

$$s = (p * \cos\theta)/t$$

where:
 θ=the gantry tilt angle value corresponding to the raw projection data associated with the image data.

* * * * *

UNITED STATES PATENT AND TRADEMARK OFFICE
CERTIFICATE OF CORRECTION

PATENT NO. : 6,229,869 B1
DATED : May 8, 2001
INVENTOR(S) : Hui Hu

It is certified that error appears in the above-identified patent and that said Letters Patent is hereby corrected as shown below:

Column 8,
Line 25, delete "z-kemel" and substitute therefore -- z-kernel --.

Column 11, claim 10,
First equation, delete "62" and substitute therefore -- $\beta$ --.

Column 12, claim 10,
Last equation, delete "529" and substitute therefore -- $\Pi$ --.

Signed and Sealed this

Twenty-sixth Day of March, 2002

Attest:

JAMES E. ROGAN
*Attesting Officer*  *Director of the United States Patent and Trademark Office*